(12) United States Patent
Bhattacharya (10) Patent No.: US 9,910,162 B2
(45) Date of Patent: Mar. 6, 2018

(54) CALIBRATING IN SINGLE PHOTON EMISSION COMPUTED TOMOGRAPHY WITH MULTI-EMISSION ENERGIES

(71) Applicant: Siemens Medical Solutions USA, Inc., Malvern, PA (US)

(72) Inventor: Manojeet Bhattacharya, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/315,151

(22) PCT Filed: Jun. 12, 2015

(86) PCT No.: PCT/IB2015/054449
§ 371 (c)(1),
(2) Date: Nov. 30, 2016

(87) PCT Pub. No.: WO2015/189809
PCT Pub. Date: Dec. 17, 2015

(65) Prior Publication Data
US 2017/0192104 A1    Jul. 6, 2017

Related U.S. Application Data

(60) Provisional application No. 62/011,066, filed on Jun. 12, 2014.

(51) Int. Cl.
*H01L 27/146* (2006.01)
*G01T 1/164* (2006.01)
(Continued)

(52) U.S. Cl.
CPC ............ *G01T 1/1647* (2013.01); *A61B 6/582* (2013.01); *G01T 1/166* (2013.01); *G01T 1/1642* (2013.01); *G01T 1/208* (2013.01); *G01T 1/247* (2013.01); *G01T 1/249* (2013.01); *G01T 1/2964* (2013.01); *G01T 1/40* (2013.01); *G01T 7/005* (2013.01); *G12B 13/00* (2013.01)

(58) Field of Classification Search
CPC ....................................................... G21H 5/02
See application file for complete search history.

(56) References Cited

U.S. PATENT DOCUMENTS 5,491,342 A    2/1996    Lim

FOREIGN PATENT DOCUMENTS

WO    2005040855    5/2005

OTHER PUBLICATIONS

Strydhorst et al., "Quantitative measurement of In Vivo tracer concentration in rats with multiplexed multi-pinhole SPECT," Jun. 2014, IEEE Transaction on Nuclear Science, vol. 61, No. 3, pp. 1136-1142.*

* cited by examiner

*Primary Examiner* — Kiho Kim (57) ABSTRACT

For calibration (24) for quantitative SPECT, a multiple energy emission source (11) is used for calibration. The planar sensitivities and/or uniformities are determined at different emission energies based on detections from the multiple energy emission source. For estimating (32) the activity concentration, sensitivities and/or uniformities based on measures (26) at different emission energies increase accuracy. The multiple energy emission source (11) may alternatively or additionally be used to calibrate (40) a dose calibrator (15).

20 Claims, 2 Drawing Sheets (51) Int. Cl.
*G12B 13/00* (2006.01)
*G01T 1/166* (2006.01)
*G01T 1/24* (2006.01)
*G01T 1/29* (2006.01)
*G01T 7/00* (2006.01)
*G01T 1/208* (2006.01)
*G01T 1/40* (2006.01)
*A61B 6/00* (2006.01)

CALIBRATING IN SINGLE PHOTON EMISSION COMPUTED TOMOGRAPHY WITH MULTI-EMISSION ENERGIES

RELATED APPLICATIONS

The present patent document claims the benefit of the filing date under 35 U.S.C. § 119(e) of Provisional U.S. Patent Application Ser. No. 62/011,066, filed Jun. 12, 2014, which is hereby incorporated by reference.

BACKGROUND

The present embodiments relate to calibration for single photon emission computed tomography (SPECT). Sensitivity and/or uniformity of the gamma camera are calibrated.

Calibration is provided for quantitative SPECT imaging. SPECT imaging uses a radiotracer to determine metabolic function within a patient. For example, the uptake of the radiotracer by tissues in the body is measured. Counts of emissions from the radiotracer are detected. The activity concentration of the radiotracer from different locations is reconstructed from the detected emissions. The reconstruction uses the sensitivity and uniformity of the detector. If a class standard sensitivity or uniformity is used, the detector-specific sensitivity or uniformity may be different, contributing a possible source of error in quantitative SPECT imaging.

System-specific sensitivity may be provided using a dose calibrator. The sensitivity of the detector is measured using a source at one energy and an activity of the source measured with the dose calibrator. The dose calibrator may introduce uncertainty, especially where the radioisotope used for the patient scan is at a different energy than the source. Similarly, a sheet source for measuring uniformity corrections may be at a different energy than the radioisotope used for the patient scan. Since the uniformity is emission energy dependent, this difference in energy may introduce uncertainty.

BRIEF SUMMARY

By way of introduction, the preferred embodiments described below include methods, systems, and non-transitory computer readable media for calibration for quantitative SPECT. A multiple energy emission source is used for calibration. The planar sensitivities and/or uniformities are determined at different emission energies based on detections from the multiple energy emission source. For estimating the activity concentration, sensitivities and/or uniformities based on measures at different emission energies increase accuracy. The multiple energy emission source may alternatively or additionally be used to calibrate a dose calibrator.

In a first aspect, a method is provided for calibration for quantitative SPECT. A first system-specific planar sensitivity or a first system-specific uniformity of a gamma camera to a calibration source is measured for a first energy. The calibration source has multiple emission energy peaks including the first energy and a second energy. A second system-specific planar sensitivity or a second system-specific uniformity of the gamma camera to the calibration source is measured for the second energy. Activity concentration of a liquid radiotracer is estimated as a function of the first and second system-specific planar sensitivities or the first and second system-specific uniformities.

In a second aspect, a method is provided for calibration for quantitative SPECT. A long-lived source is positioned by a detector of a SPECT system. The long-lived source has multiple emission energies. A detector detects emissions at the multiple emission energies by the long-lived source. The detector of the SPECT system is calibrated as a function of the emissions at the multiple emission energies by the long-lived source.

In a third aspect, a system is provided for calibration in SPECT imaging. A long-lived point source is operable to generate emissions at two or more peak energies between 50 keV and 400 keV. The long-lived point source is positioned in a dose calibrator. A processor is configured to determine a correction as a function of energy for the dose calibrator and from measures by the dose calibrator of the emissions at the two or more peak energies of the long-lived point source.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

System-specific sensitivities and/or uniformities of a gamma camera to a factory calibrated long-lived point source are measured for different energies of emission. System-specific sensitivity and/or uniformity calibration over a plurality of different gamma ray energies provides calibration more specific to any of various clinically relevant isotope emission energies.

Calibration isotopes with emissions at multiple energies are prepared. The calibration isotopes are used to calibrate planar sensitivity of the gamma camera at multiple emission energies when used in an isotropic point source form. The calibration isotopes are used to perform extrinsic uniformity calibration at multiple emission energies and also for multiple collimators when used in the form of a sheet source. In one approach for a calibration isotope with emissions at multiple energies, an "isotope cocktail" is prepared from long-lived (e.g., t½>3 months) single emission isotopes. The relative amounts of individual isotopes are chosen based on their specific activities and minimum count rate requirements on acquisition times. In another approach, a single isotope has multiple well-spaced (e.g., 100 keV spacing) emission lines. The single isotope is chosen to have an activity that is determined by its specific activity acquisition time requirements. In yet another approach, a dose calibrator is calibrated using the isotope cocktail or the single isotope with multiple well-spaced emission lines.

Figure 1:
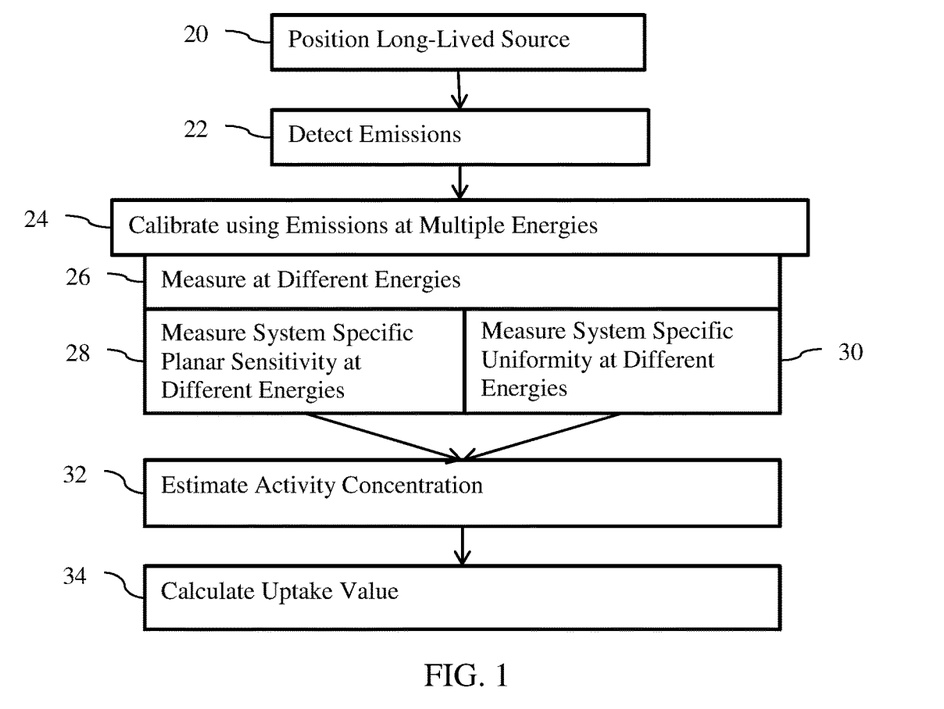
FIG. 1 is a flow chart diagram of one embodiment of a method for calibration in quantitative SPECT.

FIG. 1 shows one embodiment of a method for calibration in quantitative single photon emission computed tomography (SPECT). For activity concentration estimation, the planar sensitivity and/or uniformity of the gamma camera are determined. The planar sensitivity and/or uniformity are for the emission energy of the radiotracer used in the patient. To more likely provide accurate, system-specific calibration, the calibrations is performed using a multiple energy emission source. For uptake calculation (e.g., specific uptake value calculation), the dose from the liquid radiotracer used in the patient is also calibrated in a way removing variability due to both dose and gamma camera.

The method is applied for a given SPECT system. The sensitivity and/or uniformity of the specific gamma camera are measured. The measurements are performed regularly, such as part of monthly or other period calibration of the SPECT system. The measurements may be performed upon an identified need, such as change or damage to the collimator or detector of the gamma camera.

Additional, different, or fewer acts may be performed. For example, acts 20, 22, 32, and/or 34 are not provided. As another example, acts 28 is performed without act 30, or act 30 is performed without act 28. Only one or both of the planar sensitivity and the uniformity are measured with a calibration source emitting at multiple energies. In other examples, acts related to positioning the patient, configuring the SPECT scanner, and/or SPECT imaging are provided.

The acts are performed in the order shown or a different order. For example, act 26 is performed before each of acts 28 or 30 in sequence (e.g., act 26, then act 28, then act 26, and then act 30).

In act 20, a calibration source of gamma radiation is positioned at a fixed distance (e.g., 20 cm) from the gamma camera. Any distance may be used. The calibration source is an isotropic point source for measuring planar sensitivity. The calibration source is a sheet source for measuring uniformity. Other types of sources may be used.

The calibration source is a long-lived, factory-calibrated source. The radioisotope of the calibration source is long lived relative to the radioisotope ingested by or used for emitting gamma rays from the patient. If the half-life of the radioisotope is long enough (e.g., greater than 2 months, 3 months, 6 months, 1 year, or more), then frequent replacement of the calibration source is avoided. The half-life is not so long that the specific activity is too low for a calibration source (e.g., less than 1 mCi/µg).

The calibration source has emissions at different energies. Energies at two or more levels are emitted. The multiple emission energy peaks are used for calibration. The energies are close to or similar to emission energies used for clinical radiotracers, such as being within 50-400 keV. The emissions of the calibration source have significant strength or substantial branching ratio (e.g., 2, 10, 20, 50 or higher) so that measurements may be performed in a reasonable time (e.g., less than 1 hour). The energies are sparse (e.g., few number of detector separable peaks). The highest energy is less than 400 keV for the primary peaks, but may be greater.

In one embodiment, the emissions are generated by two or more radiotracers. The calibration source is formed with a mix of different isotopes. Each radiotracer causes emissions at a different energy, so the mix has one isotope emitting at one energy and another isotope emitting at another energy. More than two isotopes may be used, providing a calibration source with peak energy emissions at three or more energies. In one example mix, 139Ce and 113Sn are mixed, providing half-lives of 137.6 days and 115.1 days, e-gamma of (a) 165.9 and (b) 255.1 and 391.7, and branching ratio of (a) 80.0 and (b) 2.1 and 65.0. Other isotopes may be used. In this example, one of the isotopes of the mix has two major energy peaks, providing three energy peaks for the mix of two isotopes.

In another embodiment, a radionuclide with different emission energies is used without being in a mix. The calibration source is formed with an isotope having multiple primary or major emission energy peaks or lines. For example, the isotope is 101Rh with a half-life of 3.3 years, e-gamma of 127.2, 198.0, and 325.2 and respective branching ratios of 68.0, 73.0, and 11.8. Other multi-emission isotopes may be used.

In act 22, the gamma camera detects emissions. Emissions from the calibrations source are detected over time. The gamma camera includes a collimator through which some emissions pass, and a detector that converts the emissions into data. The collimator in front of the detector limits the direction of photons detected by the SPECT detector, so each detected emission is associated with an energy and line or cone of possible locations from which the emission occurred. The lateral position of the line or cone relative to the detector may likewise be determined. The SPECT detector includes photomultiplier tubes or other photon detectors layered with a scintillation crystal. The photomultiplier tubes are arranged along a rectangular or other grid to provide a two-dimensional planar array for detecting gamma radiation. Other types of detectors may be used, such as any gamma detector.

Emissions from the long-lived calibration source are detected. The detector detects the emissions, including detecting a location on the planar gamma camera and an energy of the detected emission. Counts of detected gamma photons are collected by the detectors.

The counts are obtained for different energy or acquisition windows. For each energy of the calibration source, a count is made. Any size window or energy range may be used, such as 20% of the peak energy. Emissions within the energy window are included in the count. Counts are provided for each of two or more energy windows to count emissions from the same calibration source at a same time. The planar sensitivity and/or uniformity are energy dependent, so the separate counts for the separate energies are used to determine the planar sensitivity and/or uniformity for different energies.

In act 24, the gamma camera of the SPECT system is calibrated as a function of the emissions at the multiple emission energy levels of the long-lived source. In general, the sensitivity (planar and/or uniformity) are measured for different emission energies. The sensitivities for the different emission energies of the calibration source are determined for calibration.

The calibration is for an emission energy of the radiotracer used with the patient, so the pool of available calibrations sensitivities are used to find a closest emission energy, surrounding emission energies, or all of the emission energies of the calibration. The planar sensitivity and/or uniformity for the emission energy of the radiotracer is derived, at least in part, from the available set of planar sensitivities and/or uniformities measured with the calibration source. The calibration source sensitivities (planar and/or uniformity) are used with any of various radiotracer emission energies. The measured sensitivities to the different energies of the calibration source allow for more accurate calibration to any energy level of any radiotracer.

A processor calibrates, such as measuring the sensitivities from the detector counts and a looked-up or known activity concentration of the calibration source. The calibration of act 24 is shown as being performed with acts 26, 28 and 30. Additional, different or fewer acts may be used, such as not performing one of acts 28 or 30.

In act 26, the system-specific (i.e., specific gamma camera being used) planar sensitivity and/or uniformity are measured at each of two or more emission energies. In the example multi-energy isotope or mix above, the planar sensitivity and uniformity are measured at each of three emission energies.

For planar sensitivity in act 28, the time from the first or initial count to a given number of counts is determined. The sensitivity is the number of counts divided by the time and the dose of the calibration source. The dose or activity concentration of the calibration source is known. Other calculations of sensitivity may be used. The sensitivity to the point source provides an overall or gamma camera planar sensitivity.

The planar sensitivity is measured for two or more energies. The total number of counts per unit time (i.e., count rate) from the isotropic point source is measured at each energy. These count rates for the different energies are the same or different. The count rates are divided by the activity concentration of the calibration source, providing sensitivities as a function of energy.

For use in quantitative SPECT for a given patient, a planar sensitivity is used in reconstruction. The patient ingests or is injected with a radioisotope at a given energy. The radioisotope has a same energy as one of the energies or different from all of the energies of the calibration source. For a matching energy, the planar sensitivity for that matching emission energy is used. For a non-matching energy, the planar sensitivity for the closest emission energy of the calibration source is used. Alternatively, a weighted interpolation is performed on the planar sensitivities from the closest higher and lower energies from the calibration source to the energy of the radiotracer for the patient.

As an alternative, a class-standard for the gamma camera is used in combination with the system-specific planar sensitivities from the calibration source. A class-standard planar sensitivity of the gamma camera to the radiotracer is adjusted or altered based on a difference of a class-standard planar sensitivity at a calibration source energy to the measured planar sensitivity at that energy. The set of measures from the calibrations source at different energies is used as discussed above to find a closest one or ones to the energy of the radiotracer.

Any class or grouping may be used, such as defining a class as a given construction (e.g., materials and array configuration) with or without a specific collimator and/or scintillator crystals. For a given class, a number of different gamma cameras are manufactured to be used in a respective number of different SPECT systems. Different types of SPECT systems may use the same or different class of detectors.

The class of detectors has a class sensitivity to radiation sources. Different classes have different sensitivities. Within a class, given detectors may have different sensitivities, but generally have similar sensitivities. For a class sensitivity, the average sensitivity is calculated from measurements by any number (e.g., tens or hundreds) of members of the class.

Class standard planar sensitivities are measured for the energies of the factory calibrated long-lived point source and for the radiotracer used for the patient. A difference in planar sensitivity of the class-standard for the calibration source from the measured system-specific planar sensitivity is determined. The difference is a ratio, percentage, or absolute value. By having the system-specific planar sensitivities at different energies, a range of planar sensitivities are available to use with any of various radiotracers. The difference for a closest calibration source energy to the energy of the radiotracer may be selected. Multiple differences may be determined, such as one for each emission energy of the calibration source, or one for the closest higher and lower energies of the calibration source to the energy of the radiotracer.

The class-standard planar sensitivity for the radiotracer is altered as a function of the difference or differences. For example, a closest calibration source energy has a difference from the class standard of 2% less. As another example, a weighted interpolation or curve fitting to the planar sensitivities of the various energies of the calibration source indicate a difference of 2% less at the radiotracer energy. The class-standard planar sensitivity of the radiotracer is reduced by 2% to provide a system-specific planar sensitivity.

For calibrating uniformity in act 30, the calibration is a function of the energy. For uniformity, the sensitivity varies as a function of location on the gamma camera or detector. Location specific sensitivity is calculated from the location specific counts. The sheet source emits uniformly (e.g., within a 10% tolerance) to each of the different locations on the planar detector. The sensitivity of different locations on the detector is calculated.

The sensitivity varies across the gamma camera. Different locations have different sensitivities. A sensitivity at a reference location, an average sensitivity, or the planar sensitivity is used as a reference. The processor calculates a difference from the reference in the sensitivity at each location. The collection of differences as a function of location is the uniformity. The differences are weights to be applied as a function of location to counts of emissions detected from a patient. Other measures of variance may be used. Other representation of uniformity may be used, such as a fit surface to the differences or the location specific sensitivities themselves.

Since the sheet source emits at different energies, the uniformity is measured at each of the different energies. For a given energy, one uniformity set of location-specific sensitivities are measured. For a different energy, another uniformity set of location-specific sensitivities are measured. Uniformity is provided for each of any number of emission energies. The uniformities at the different emission energies are the same or different. Location-specific sensitivity is measured across the gamma camera for the different energies of the calibration source.

For use with a given radiotracer and patient, the uniformity used is a function of the uniformities from the different energies of the calibration source. The uniformity measured for the closest calibration source energy to the radiotracer energy is used. Alternatively, a curve is fit for the weight at each location as a function of energy. The weight for each location at the energy of the radiotracer is selected from the curves to create the uniformity for the radiotracer energy. In another approach, the nearest higher and lower calibration energies to the radiotracer energy are selected. The uniformity for the radiotracer energy is interpolated from the uniformities for the selected calibration energies. In yet another approach, a deviation from class-standards is used.

The uniformities are extrinsic uniformities. For the measurements at the different energies, both the collimator and detector of the gamma camera are used. In other embodiments, the uniformities are intrinsic uniformities measured without the collimator. In one embodiment, geometric collimator correction matrices are determined for each of a plurality of different collimators that are used with a given detector. The intrinsic uniformity is factored from the extrinsic uniformity using each collimator, providing the respective collimator correction matrices. For a given calibration, the current extrinsic uniformity is determined from a measured intrinsic uniformity and the known or stored collimator correction matrix. Separate intrinsic uniformity and collimator correction matrix are used for reconstruction. Alternatively, the extrinsic uniformity is used.

In act 32, the activity concentration is estimated. The activity concentration in a patient having received the liquid radiotracer is determined as part of reconstruction by a processor of the SPECT imaging system. After ingesting or injecting the radiotracer into the patient, the patient is positioned relative to the detector and/or the detector is positioned relative to the patient. Emissions from the radiotracer within the patient are detected over time. The count and/or count rate are determined. To determine the locations within the patient at which the emissions occurred, the detected emissions are reconstructed into an object space.

For reconstruction, the activity concentration (e.g., quantitative SPECT) is reconstructed using a system matrix or forward projection modeling system effects. Distribution of emissions in a volume or image data is reconstructed from the detected emissions. The quantity or amount of uptake for each location (e.g., voxel) is estimated from the counts as part of the reconstruction in computed tomography. The SPECT imaging system estimates the activity concentration of an injected radiopharmaceutical or tracer for the different locations. In quantitative SPECT, the goal is to estimate the activity concentration in kBq/ml of the tracer (i.e., isotope) that was injected into and distributed within the patient.

The reconstruction is iterative and contains a model of the imaging formation physics as a pre-requisite of quantitative reconstruction. The image formation model includes the detected data (e.g., counts), the system matrix or forward projection, isotope properties (e.g., corrected dose value), and biology. The system matrix or forward projection represents mechanical properties of system, including the planar sensitivity and/or uniformity. The system matrix or forward projection may include other information (e.g., injection time and patient weight as represented by SUV).

Reconstruction includes a projection operator that is able to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach.

The reconstruction uses the system matrix or forward projection representing various aspects of the detection of the emissions, including modeling the imaging physics. The imaging physics includes aspects of the SPECT system, such as calibration of the SPECT system. The system matrix or forward projection includes the detector sensitivity, such as the system-specific planar sensitivity and/or uniformity to the liquid radiotracer used in the patient. The system-specific planar sensitivity and/or uniformity are used in the estimation of the activity concentration. Using the system-specific planar sensitivity and/or system-specific uniformity for activity concentration estimation by the reconstruction engine may produce activity concentrations that are accurate and free of or less responsive to camera specific variations.

The activity concentration is a function of the system-specific planar sensitivities and/or uniformities from the different energies of the calibration source. The planar sensitivities and/or uniformities are measured for each energy. This pool is used for selecting based on closest calibrator energy to the radiotracer energy. A single member of the pool or set is selected, or multiple members are selected for interpolation. In another approach, curve fitting to all of the members of the pool is used to estimate the planar sensitivity and/or uniformity at any energy. In yet another approach, the members of the pool are used to determine deviation from class standard, and the deviation is then applied to a class standard for the radiotracer.

In act 34, the processor calculates specific uptake values (SUVs). SUVs are the activity concentration as a function of the dose of the radiotracer. The dose indicated by a provider may be corrected, such as through calibration or measurement with a dose calibrator. The activity concentration represents the amount of uptake at each location. This amount of uptake is a measure of emitted radiation, so is not normalized for the radiation dose provided to the patient. As a result, comparing uptake from different times may not be useful unless the same dose is provided. By calculating the SUV, uptake normalized for dose is provided, allowing comparison of different measures. The activity concentration is divided by the injected dose. Other functions may be used. For example, the SUV may be a function of the body mass or other physical characteristic of the patient. The uptake magnitude represented in the activity concentration is normalized for both dose and body mass.

The dose is included as part of the system matrix or forward projector or as separate isotope data used in reconstruction. Alternatively, the SUV is calculated from reconstructed activity concentration.

Figure 2:
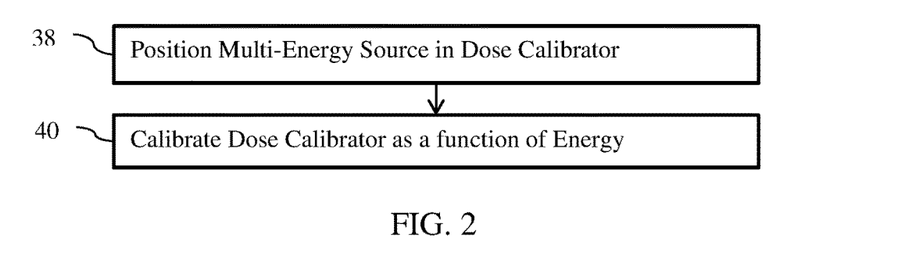
FIG. 2 is a flow chart diagram of one embodiment of a method for calibration of a dose calibrator.

FIG. 2 shows another method for calibration in SPECT with a calibration source having multiple energies. In addition or alternative to planar sensitivity and/or uniformity calibration, the dose calibrator is calibrated. The dose calibrator is an ion chamber or other vessel for measuring activity of the radiotracer. The measures of the dose calibrator may be emission energy dependent.

In act 38, the multi-energy calibration source with the long-lived radioisotope or radioisotopes is positioned in the dose calibrator. For example, the isotropic point source is placed in the dose calibrator.

In act 40, the dose calibrator is calibrated with the calibration source. The activity concentration of the calibration source is known. The dose calibrator measures the activity. A processor calculates a difference between the known activity concentration and the measured activity concentration. This difference is used to weight or adjust measures from the dose calibrator of the injected activity of a radiotracer.

By using the calibration source with multiple energies in a range similar to radiotracer energies, the calibration of the dose calibrator may be more accurate in the relevant range. For example, the emissions from the calibration source are between 50-400 keV instead of being 122 keV and 1.4 meV. When the dose calibrator is used to measure activity of the radiotracer, the measured activity, as adjusted for the calibration, may be more accurate. The activity value is used in calculating SUV from the activity concentration.

Figure 3:
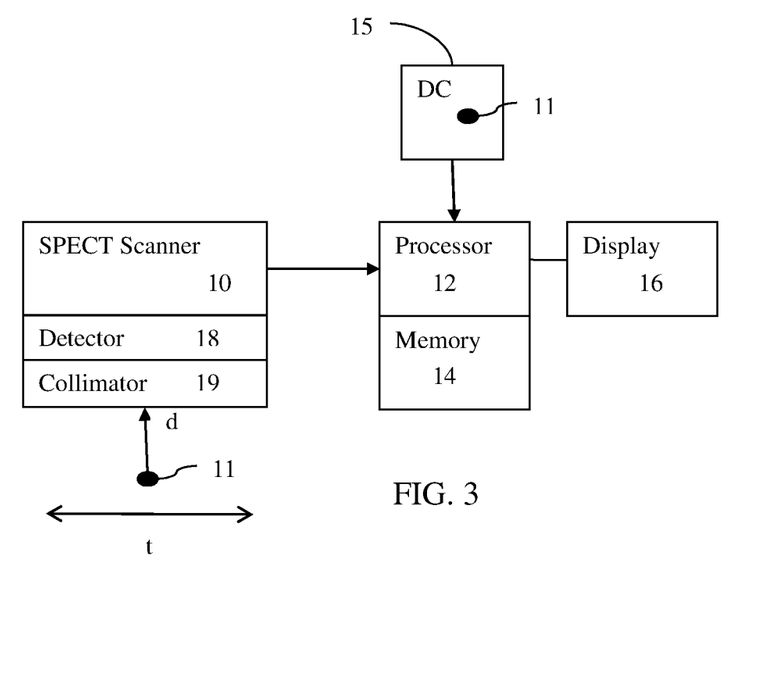
FIG. 3 is a block diagram of a system, according to one embodiment, for calibration in SPECT imaging.

FIG. 3 shows one embodiment of a system for calibration in SPECT imaging. The system includes an SPECT scanner 10, a processor 12, a memory 14, and a display 16. The processor 12, memory 14, and/or display 16 are part of the SPECT scanner 10 or are separate (e.g., a computer or workstation). Additional, different, or fewer components may be provided. For example, the system is a computer without the SPECT scanner 10. As another example, user input, patient bed, or other SPECT related devices are provided. Other parts of the system may include power supplies, communications systems, and user interface systems.

The SPECT scanner 10 is a SPECT system. As a SPECT system, a detector 18 and a collimator 19 are provided. Other components may be provided. Any now known or later developed SPECT scanner 10 may be used.

The detector 18 is a gamma camera connected with a gantry. The gamma camera is a planar photon detector, such as having crystals or scintillators with photomultiplier tubes or other optical detector. The gantry rotates the gamma camera about the patient. During scanning of a patient, emission events are detected with the camera at different positions or angles relative to the patient. For sensitivity measurements from a calibration source 11 (e.g., point or sheet source) at a distanced from the detector 18, the gamma camera may be stationary.

The gamma camera includes the collimator 19. The collimator 19 is lead, tungsten, or other gamma ray impervious material. The collimator 19 includes holes or other structures for limiting the angle of incidence of gamma rays on the detector 18. Any now known or later developed collimator 19 may be used.

The SPECT scanner 10, using the detector 18, detects emissions from the calibration source 11 for measuring system specific sensitivity. As a point source, the calibration source 11 may be at any position in the 2D transverse direction, t, relative to the detector 18, but is preferably centered. As a sheet source, the calibration source 11 is positioned so that emissions from the source may be detected at all locations on the detector 18 given the collimator 19. The emissions are measured with the calibration source 11 at any distance, d.

The calibration source 11 is a long-lived, factory-calibrated source. Any size point source may be used, such as a 1 mm$^3$ vessel, with the long-lived radioisotope. Any thickness, size, or shape may be used for the sheet source. The dose of the calibration source 11 is known with any degree of accuracy. The dose is measured at a factory with equipment having greater accuracy than used in labs providing liquid radiotracers. Any now known or later developed source may be used. The calibration source 11 is formed from one or more radioisotopes to emit at different energies or with different energy peaks. A mix of different radioisotopes and/or a radioisotope that emits at multiple energies may be used. The calibration source 11 is positioned relative to the detector 18 for measuring detector or system-specific sensitivity (e.g., planar sensitivity or uniformity).

The SPECT scanner 10 may include a timer. The timer measures a period from activation of detection through to reaching a number of counts. The emission events detected by the detector 18 are counted over time to calculate the sensitivity. The SPECT scanner 10, using the processor 12 or another processor, is configured to measure the system-specific sensitivities (e.g., planar sensitivities and/or uniformities) of the detector 18 to the long-lived calibration source 11 at different emission energies.

For imaging uptake or activity concentration in a patient, the detector 18 detects emissions from the patient. The emissions occur from any location in a finite source (i.e., the patient). The radiotracer in the patient migrates to, connects with, or otherwise concentrates at specific types of tissue or locations associated with specific biochemical reactions. As a result, a greater number of emissions occur from locations of that type of tissue or reaction. For example, the radiotracer is designed to link with locations of glucose uptake, fatty acid synthesis, or other metabolic process.

The SPECT scanner 10, using the processor 12 or another processor, is configured to reconstruct the imaged volume by applying a system matrix to the detected data. Any reconstruction may be used to estimate the activity concentration in the patient. The processor 12 is used to perform the reconstruction, or the SPECT scanner 10 has another processor that performs the reconstruction. The SPECT scanner 10 accesses the detected emission events from the memory 14 or buffers to reconstruct. The system matrix or forward projection includes a system-specific planar sensitivity and/or uniformity for the liquid radiotracer provided to the patient. This planar sensitivity and/or uniformity are determined by the processor 12 from the measured planar sensitivities and/or uniformities at the different energies of the calibration source 11. The radiotracer system-specific planar sensitivity and/or uniformity are used for the reconstruction. The reconstruction may also use a dose value for the radiotracer applied to the patient.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another for calculating planar sensitivity and/or uniformity. In one embodiment, the processor 12 is a control processor or other processor of SPECT scanner 10. In other embodiments, the processor 12 is part of a separate workstation or computer.

The processor 12 operates pursuant to stored instructions to perform various acts described herein, such as calibrating of act 24, estimation of activity concentration of act 32 and/or uptake value calculation of act 34. The processor 12 may control the performance of act 22. A person or robot may perform act 20 of FIG. 1 or act 38 of FIG. 2. The processor 12 is configured by software and/or hardware to perform, control performance, and/or receive data resulting from any or all of the acts of FIG. 1 and/or FIG. 2.

In one embodiment, the processor 12 is configured receive counts or count rates from a detector and measure system-specific planar sensitivities and/or uniformities from the count or time to reach a count. The activity concentration of the calibrator source is known or accessed from the memory, so that the SPECT scanner 10 is calibrated by the processor 12 using the system-specific planar sensitivities and/or uniformities at different energies. The processor 12 determines the planar sensitivity and/or uniformity to use for a given patient or radiotracer based on measures at different energies.

The detected emission events or other scan data is stored in the memory 14. The data is stored in any format. The memory 14 is a buffer, cache, RAM, removable media, hard drive, magnetic, optical, database, or other now known or later developed memory. The memory 14 is a single device or group of two or more devices. The memory 14 is part of SPECT scanner 10 or a remote workstation or database, such as a PACS memory.

The memory 14 stores the dose of the calibrator source 11, measured system-specific planar sensitivities at different energies, and/or measured system-specific uniformities at different energies. The memory 14 may store data at different stages of processing, such as counts, time to reach a count, raw data representing detected events without further processing, filtered or thresholded data prior to reconstruction, reconstructed data, filtered reconstruction data, system matrix, projection data, thresholds, an image to be displayed, an already displayed image, or other data. The memory 14 or a different memory may store class standard sensitivities loaded into or provided to the SPECT scanner 10. The memory 14 or a different memory stores any calibration information. For processing, the data bypasses the memory 14, is temporarily stored in the memory 14, or is loaded from the memory 14.

The memory 14 is additionally or alternatively a non-transitory computer readable storage medium with processing instructions. The memory 14 stores data representing instructions executable by the programmed processor 12. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 16 is a CRT, LCD, plasma screen, projector, printer, or other output device for showing an image. The display 16 displays an image of the reconstructed functional volume, such as showing activity concentration as a function of location. The uptake function of the tissues of the patient is represented in the image. Multiplanar reconstruction, 3D rendering, or cross-section imaging may be used to generate the image from the voxels of the reconstructed volume. Alternatively or additionally, any quantities derived by the processor 12 may be displayed, such as SUVs and/or change in SUV. Other quantities may be determined, such as average SUV or activity concentration for a region, maximum SUV, peak SUV in a predetermined unit volume, variance in activity concentration, or total SUV.

The dose calibrator 15 is an ion chamber or other vessel for measuring dose. The dose calibrator 15 is shown connected to the processor 12 of the SPECT scanner 10, but may instead have its own processor or connect to a computer with another processor. The SPECT scanner 10 may not be provided.

The long-lived source 11 in the form of a point source is positioned in the dose calibrator 15. The source 11 is the same or a different source 11 used for calibrating the SPECT scanner 10. The source 11 generates emissions at two or more peak energies between 50 keV and 400 keV. These energies are similar to energies used for clinical SPECT imaging.

The processor 12 is configured to determine a correction as a function of energy for the dose calibrator 15. The emissions from the source 11 are measured. The emissions are at the different energy peaks. The measured emissions from the dose calibrator 15 are received by the processor 12. The processor 12 determines a difference in the measured activity concentration by the dose calibrator 15 with a known activity concentration of the source 11. The difference is used as a correction by the processor 12 for calibration of other measures by the dose calibrator 15.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for calibration for quantitative single photon emission computed tomography (SPECT), the method comprising:
    measuring (26), for a first energy, a first system-specific planar sensitivity or a first system-specific uniformity of a gamma camera to a calibration source, the calibration source having multiple emission energy peaks including the first energy and a second energy;
    measuring (26), for the second energy, a second system-specific planar sensitivity or a second system-specific uniformity of the gamma camera to the calibration source; and
    estimating (32) activity concentration of a liquid radiotracer as a function of the first and second system-specific planar sensitivities or the first and second system-specific uniformities.

2. The method of claim 1 wherein estimating (32) the activity concentration comprises selecting the first or second system-specific planar sensitivity or uniformity with a closest of the first and second energies to a radiotracer energy of the liquid radiotracer.

3. The method of claim 1 wherein estimating (32) the activity concentration comprises interpolating from the first and second system-specific planar sensitivity or uniformity based on a radiotracer energy of the liquid radiotracer.

4. The method of claim 1 wherein estimating (32) the activity concentration comprises reconstructing the activity concentration from counts measured with the gamma camera from the liquid radiotracer in the patient, the reconstructing being a function of a system matrix including a system-specific planar sensitivity term or uniformity term.

5. The method of claim 1 further comprising calculating (34) specific uptake values as a function of the activity concentration and a corrected dose value of the liquid radiotracer.

6. The method of claim 1 further comprises measuring (26), for a third energy of the calibration source, a third system-specific planar sensitivity or a third system-specific uniformity of the gamma camera to the calibration source, wherein estimating (32) comprises estimating (32) as a function of the third system-specific planar sensitivity or uniformity.

7. The method of claim 1 wherein measuring (26) for the first and second energies comprises measuring with a mix of different isotopes in the calibration source, a first of the isotopes emitting at the first energy and a second of the isotopes emitting at the second energy.

8. The method of claim 1 wherein measuring (26) for the first and second energies comprises measuring with a single isotope having the multiple emission energy peaks.

9. The method of claim 1 wherein measuring (26) for the first and second energies comprises measuring the first and second system-specific planar sensitivities, the calibration source comprising an isotropic point source (11).

10. The method of claim 9 wherein estimating (32) the activity concentration comprises altering a class-standard planar sensitivity for the liquid radiotracer as a function of a difference of a class-standard sensitivity at the first or second energy from the measured first or second system-specific planar sensitivities, respectively.

11. The method of claim 9 wherein measuring (26) the first and second system specific planar sensitivities comprises measuring first and second total number of counts and first and second times to acquire the first and second number of counts with a dose known for the calibration source.

12. The method of claim 1 wherein measuring (26) for the first and second energies comprises measuring the first and second system-specific uniformities, the calibration source comprising a sheet source.

13. The method of claim 12 wherein measuring (26) the first and second system-specific uniformities comprises measuring location-specific sensitivity across the gamma camera for the first and second energies.

14. The method of claim 12 wherein measuring (26) the first and second system-specific uniformities comprises measuring first and second extrinsic uniformity corrections, respectively.

15. The method of claim 14 further comprising determining (24) geometric collimator correction matrices for each of a plurality of collimators for the gamma camera, the determining being a function of the first and second extrinsic uniformity corrections.

16. The method of claim 1 further comprising calibrating (40) a dose calibrator (15) with the calibration source.

17. A method for calibration for quantitative single photon emission computed tomography (SPECT), the method comprising:
    positioning (20) a long-lived source by a detector of a SPECT system, the long-lived source having multiple emission energies;
    detecting (22), by the detector, emissions at the multiple emission energies by the long-lived source; and
    calibrating (40) the detector of the SPECT system as a function of the emissions at the multiple emission energies by the long-lived source.

18. The method of claim 17 wherein calibrating (40) the detector comprises calibrating (40) a planar sensitivity of the detector as a function of energy.

19. The method of claim 17 wherein calibrating (40) the detector comprises calibrating (40) a uniformity of the detector as a function of energy.

20. A system for calibration in single photon emission computed tomography (SPECT) imaging, the system comprising:
    a dose calibrator (15);
    a long-lived point source (11) operable to generate emissions at two or more peak energies between 50 keV and 400 keV, the long-lived point source (11) positioned in the dose calibrator (15); and
    a processor (12) configured to determine a correction as a function of energy for the dose calibrator (15) and from measures by the dose calibrator (15) of the emissions at the two or more peak energies of the long-lived point source (11).

* * * * *